United States Patent [19]
Volk

[11] Patent Number: 5,805,269
[45] Date of Patent: Sep. 8, 1998

[54] HIGH MAGNIFICATION INDIRECT OPHTHALMOSCOPY LENS DEVICE

[75] Inventor: Donald A. Volk, Mentor, Ohio

[73] Assignee: Volk Optical, Inc., Mentor, Ohio

[21] Appl. No.: 703,871

[22] Filed: Aug. 27, 1996

Related U.S. Application Data

[60] Provisional application No. 60/005,247 Oct. 11, 1995.

[51] Int. Cl.⁶ .................................................... A61B 3/00
[52] U.S. Cl. ............................................ 351/219; 351/205
[58] Field of Search .................................... 351/219, 205, 351/160 R, 159, 200

[56] References Cited

U.S. PATENT DOCUMENTS

| | | |
|---|---|---|
| 5,255,025 | 10/1993 | Volk ........................................ 351/219 |
| 5,523,810 | 6/1996 | Volk ........................................ 351/219 |
| 5,526,074 | 6/1996 | Volk ........................................ 351/219 |

*Primary Examiner*—Hung X. Dang
*Attorney, Agent, or Firm*—Spencer & Frank

[57] ABSTRACT

An indirect ophthalmoscopy lens device is provided for use with a slit-lamp or other biomicroscope for examination, laser treatment or surgical treatment of a patient's eye. The device comprises an image forming lens system for collecting and focussing light exiting a patient's eye to form a real image of the fundus of the patient's eye at a location outside the eye and anterior of the image forming lens system. An anterior lens having a convex anterior surface is disposed anterior to the image forming lens system so that the real image formed by the image forming lens system is located posterior of the convex anterior surface. The convex anterior surface of the anterior lens refracts chief rays of light ray bundles of the light exiting the patient's eye generally toward a collecting lens of the slit-lamp or other biomicroscope. An image viewed through the slit-lamp or other biomicroscope comprises a virtual image that has a positive magnification relative to the real image formed by the image forming lens system and relative to the fundus of the patient's eye.

22 Claims, 11 Drawing Sheets

HIGH MAGNIFICATION INDIRECT OPHTHALMOSCOPY LENS DEVICE

This application claims benefit USC Provisional Appln Ser. No. 60/005,247, filed Oct. 11, 1995.

BACKGROUND OF THE INVENTION

The invention relates to an indirect ophthalmoscopy lens device, of the contact and non-contact type, that provides high retinal magnification. Such devices are often used with a slit-lamp or other biomicroscope to view the magnified image.

In known indirect ophthalmoscopy lens devices, as retinal magnification is increased, the distance between the anterior end of the indirect ophthalmoscopy lens device and the real image produced by the device is also increased. As retinal magnification in such devices is increased beyond about 1.3x, the real image is produced so far anterior to the eye that the slit-lamp biomicroscope cannot accommodate enough retrograde motion to observe the image, due to its limited range of motion.

SUMMARY OF THE INVENTION

It is an object of the present invention to provide a high magnification indirect ophthalmoscopy lens device that provides increased retinal magnification over that available with known indirect ophthalmoscopy lens devices whereby the magnified retinal image is produced at a distance anterior to the. patient's eye which is still well within the range of motion of the vast majority of biomicroscopes presently utilized.

The above and other objects are accomplished in accordance with the invention by the provision of an indirect ophthalmoscopy lens device for use with a slit-lamp or other biomicroscope in an examination, laser treatment or surgical treatment of a patient's eye, comprising: an image forming lens system for collecting and focussing light exiting a patient's eye to form a real image of the fundus of the patient's eye at a location outside the eye; and an anterior lens having a convex anterior surface and being disposed anterior to the image forming lens system so that the real image formed by the image forming lens system is located posterior of the convex anterior surface, the convex anterior surface of the anterior lens refracting chief rays of respective light ray bundles of the light exiting the patient's eye generally toward a collecting lens of the slit-lamp or other biomicroscope, whereby an image viewed through the slit-lamp or other biomicroscope comprises a virtual image that has a positive magnification relative to the real image formed by the image forming lens system and relative to the fundus of the patient's eye.

In a preferred embodiment of the invention the chief rays proceeding from the image forming lens system diverge from one another toward the real image.

The real image formed by the image forming lens system may be located posterior the anterior lens or partially or wholly within the anterior lens. The virtual image is located posterior of the convex anterior surface of the anterior lens and may either be located in air posterior to the anterior lens, or partially or wholly within the anterior lens.

In the preferred embodiment of the invention, increased magnification is achieved by designing the optics of the image forming lens system and placing the image forming lens system at a given distance from the patient's eye so that the chief light rays of the light ray bundles emanating from the patient's eye and focussed by the image forming lens system to form the real image are divergent. Due in part to the extent of divergence of the chief rays, the magnification of the produced image is very high. However, peripheral regions of the magnified image would normally not be viewable because the diverging peripheral light rays would not be captured by or even directed toward the collecting lens of the slit-lamp biomicroscope. In accordance with the invention, the anterior lens bends the chief rays so that they are brought generally to a conjugate pupil area corresponding to that of the viewing slit-lamp biomicroscope. The resulting binocular and stereoscopically viewed image may be visualized through the slit-lamp biomicroscope as a further magnified virtual image that is produced posterior of (behind) the convex anterior surface of the anterior lens.

The high magnification indirect ophthalmoscopy lens device of the invention provides both high magnification and high resolution which makes it ideal for extremely detailed diagnosis and very exacting laser treatment in critical areas near the macula, which is the most light sensitive portion of the eye.

DETAILED DESCRIPTION OF THE PREFERRED EMBODIMENTS

The figures described below show respective lens layouts with overlaid ray tracings according to exemplary embodiments for implementing the principles of the invention. Although the ray tracings show light proceeding as parallel bundles from a pupil location in air, the ray tracings through the lens system follow similar pathways as do light rays which originate at the retina and proceed through the vitreous humor, crystalline lens, aqueous humor and cornea of the eye to the various lens elements of the invention embodiments. The use of parallel bundles proceeding from a pupil location in air is a simplified representation of the optical system of the emmetropic human eye and is shown represented in all optical system layouts herein. The pupil location in air in the figures is represented by the line referred to herein as pupillary plane P, with the chief rays passing through a focus centered within the pupil location. The corresponding position of the cornea "C" on an optical axis "A" in relation to the lens elements depicted is shown in FIGS. 1–4.

Figure 1:
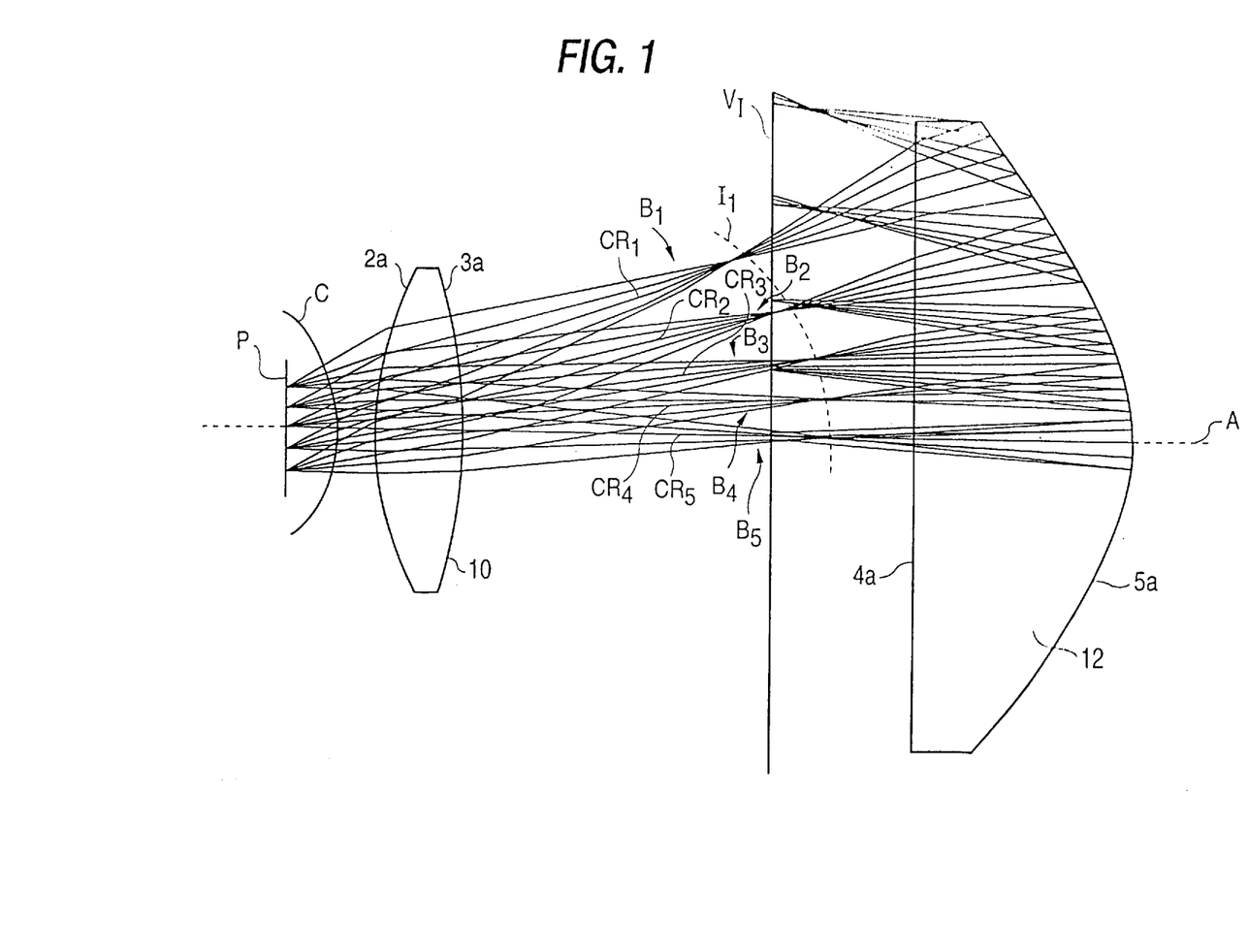
FIG. 1 is a lens layout and ray tracing of an indirect ophthalmoscopy lens device according to one embodiment of the invention.

Referring to FIG. 1, there is shown a lens layout of a first embodiment of a high magnification indirect ophthalmoscopy lens device according to the invention which includes an image forming lens comprising a biconvex first lens 10, and an plano-convex anterior lens 12 spaced in an anterior direction from lens 10 with respect to corneal surface C. First lens 10 has a convex posterior surface 2a and a convex anterior surface 3a. Anterior lens 12 has a planar posterior surface 4a and a steeply curved convex anterior surface 5a. Table I below provides an example of characteristics of the lenses, the lens surfaces, and their spacing.

TABLE I

| Surface | Radius (mm) | Conic Constant | Distance From Corneal Apex (mm) | Diameter (mm) |
| --- | --- | --- | --- | --- |
| 2a | 18.44891 | 0 | 2.000000 | 18.0 |
| 3a | 25.0 | −8.427119 | 7.000000 | 18.0 |
| 4a | Infinity | 0 | 32.000000 | 31.0 |
| 5a | 14.5 | −0.9 | 44.000000 | 31.0 |

In the above example, the lenses are both made of PMMA acrylic having an index of refraction of 1.491.

In the above Table I, Radius is the apical radius of curvature of the surface, i.e., the radius of curvature of the surface at the region at which the optical axis A intersects the surface. Although FIGS. 1, 2, 4, 5, 6, 7 & 9 show lens systems in which the lens elements are coaxially positioned, it is not a requirement of the present invention that the lens elements be so arranged. The most anterior lens element of any of the figures may be non-coaxially positioned and, in fact, may be separate and movable along and transverse to the axis of the posterior lens or lenses. Referring again to Table I, a positive apical radius as used herein denotes a convex surface and a negative apical radius denotes a concave surface. This convention is used throughout this specification. A radius of infinity denotes a planar surface. A radius having a conic constant of 0 indicates a spherical surface and a radius having a negative conic constant indicates an aspherical, conoidal surface. The column denoting Distance is the distance from the corneal apex along optical axis A. Thus, the distance between the lenses and the thicknesses of the lenses may be obtained by differencing the distances of adjacent surfaces from the corneal apex. For example, the thickness of lens 10 is 5 mm which is the difference between the distances of surfaces 2a and 3a from the corneal apex. The Diameter in Table I is the edge-to-edge distance of the lens surfaces.

FIG. 1 shows an overlaid ray tracing which results from an indirect ophthalmoscopy lens device designed according to the exemplary characteristics set forth in Table I when placed in front of an eye with surface 2a spaced 2 mm from the corneal apex. As shown in FIG. 1, light rays proceeding from pupillary plane P are collected by lens 10 and focussed to form a real image in a curved plane $I_1$ denoted by the partial dotted line connecting focal points of the respective light ray bundles B1 through B5. As can be seen, the chief rays CR1 through CR5 of the respective light ray bundles illustrated in FIG. 1 are diverging with respect to one another as they are projected toward the real image in plane $I_1$. The divergence of chief rays CR1 through CR5 can better be observed in FIG. 1A.

Figure 1A:
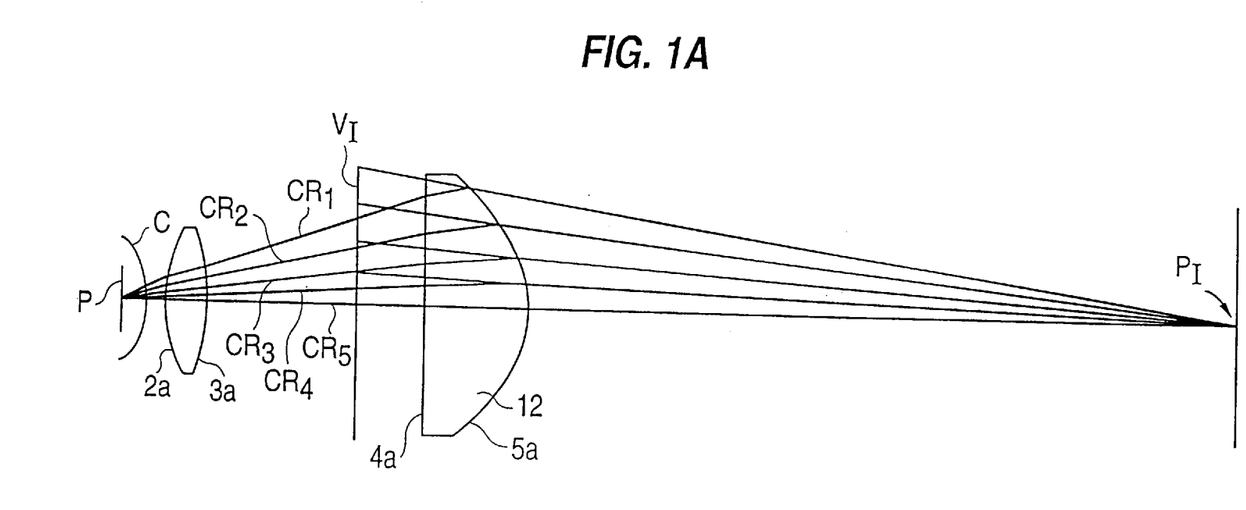
FIG. 1A is a lens layout according to the embodiment of the invention shown in FIG. 1 along with a ray tracing which shows only the chief rays which have been extended in the direction of a conjugate pupil area according to the invention.

As shown in FIG. 1A, the light rays enter anterior lens 12 and are refracted first by planar surface 4a and then by convex anterior surface 5a toward a conjugate pupil region $P_I$ which corresponds to the region of the objective lens of a slit-lamp biomicroscope (not shown) used to view the image. FIGS. 1 and 1A show that by extending the rays from the conjugate pupil $P_I$ backward and through the anterior lens 12, the rays appear to come to focus in virtual image plane $V_I$. That is, although the real image produced by first lens 10 is in the curved plane $I_1$ (FIG. 1), it appears to a person viewing the image through a slit-lamp biomicroscope, having its main collecting lens in the region of the conjugate pupil $P_I$, that the image is formed in plane $V_I$, since this is where the light ray bundles extended backwards through anterior lens 12 would appear to come to focus to form the retinal image. The virtual image in plane $V_I$ is enlarged with respect to the real image in plane $I_1$ and is also magnified with respect to the eye fundus. Using the exemplary characteristics of Table I, image plane $V_I$ will be located posterior to lens 12, at 24.108 mm from the cornea.

Figure 1B:
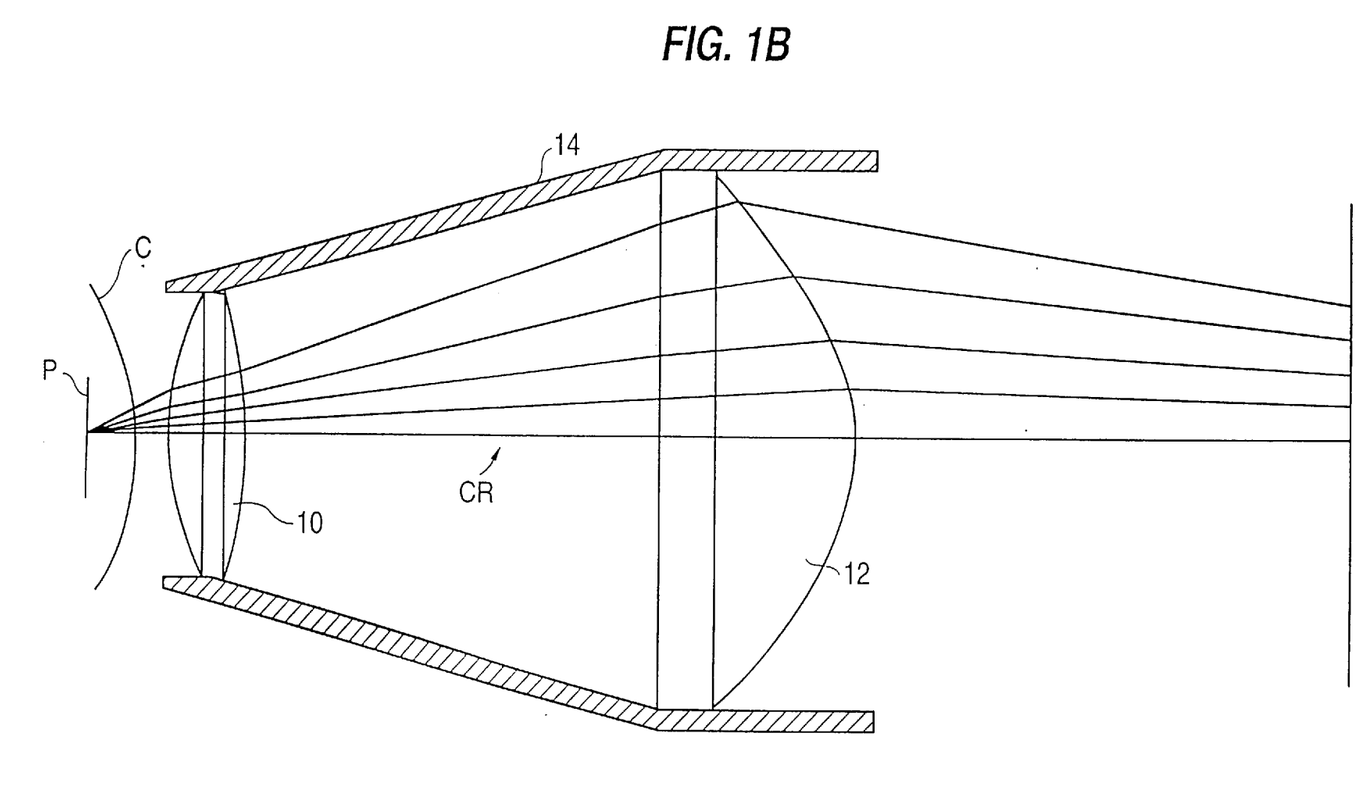
FIG. 1B is a longitudinal section of an indirect ophthalmoscopy lens device according to the embodiment of the invention illustrated in FIG. 1 including a frame for holding. the lenses of the device, together with an overlaid ray tracing of the chief rays.

FIG. 1B shows a frame or holder 14 which coaxially mounts lenses 10 and 12 of the indirect ophthalmoscopy lens device of FIG. 1. Frame 14 can be handheld between a patient's eye and a slit-lamp biomicroscope (not shown). Alternatively, the device comprising holder 14 and lenses 10 and 12 secured therein may be mounted between a patient's eye and a biomicroscope by a mounting apparatus such as that disclosed in my prior pending U.S. patent application Ser. No. 08/423,353, the disclosure of which is incorporated herein by reference.

In operation, the indirect ophthalmoscopy lens device is placed in front of a patient's eye and captures the light rays emanating from the patient's eye, represented by chief rays CR in FIG. 1B. A magnified, real image will be formed as shown in FIG. 1 in part by virtue of the divergence of the chief rays. Because the chief rays are converged generally toward the collection lens of the slit-lamp biomicroscope as shown in FIG. 1A, a person observing the image through the slit-lamp biomicroscope will view with uncompromised binocularity an even further magnified virtual image in plane $V_I$ (FIGS. 1 and 1A) as previously discussed.

Figure 2:
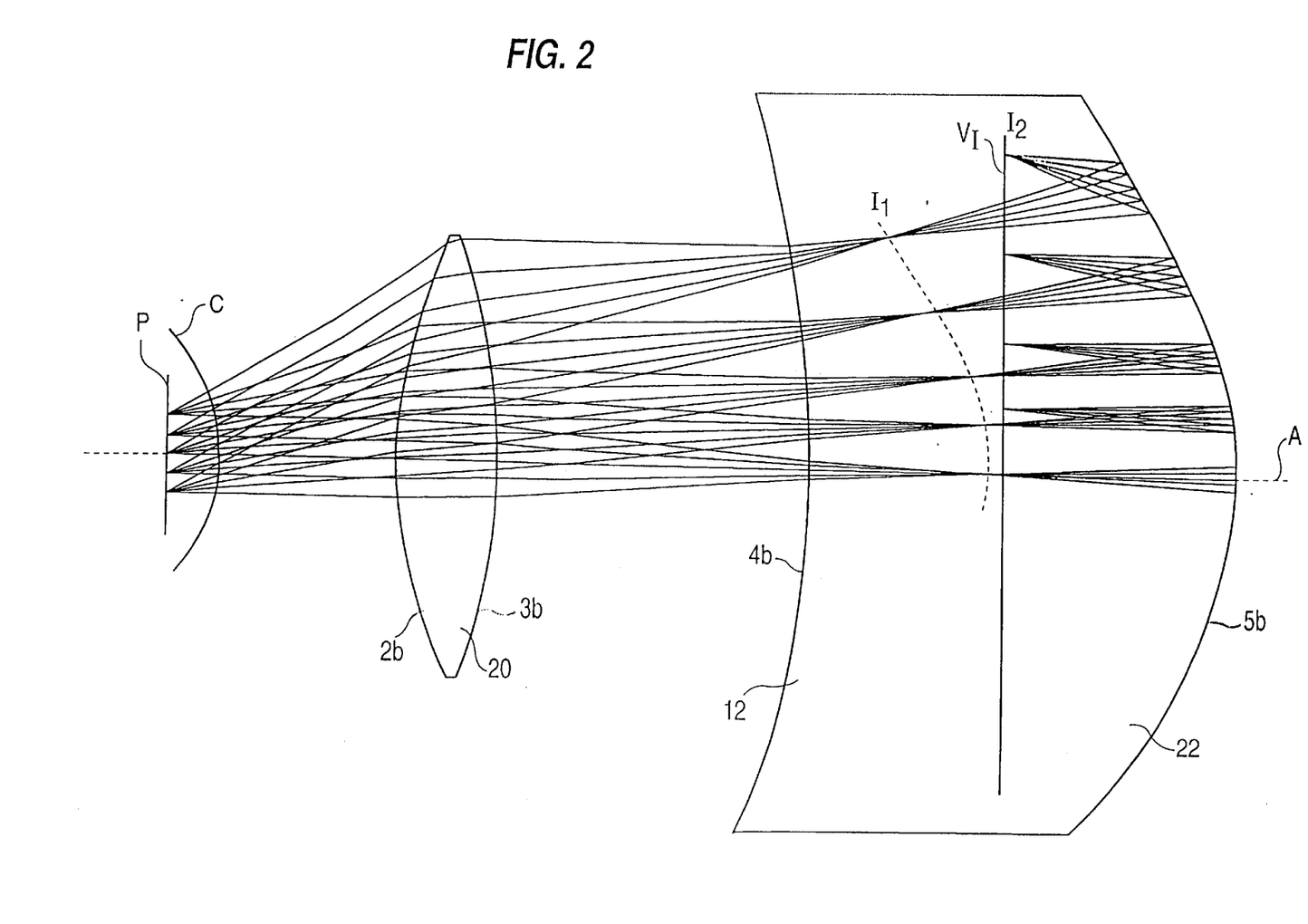
FIGS. 2 to 9 show respective lens layouts and ray tracings of indirect ophthalmoscopy lens devices according to further embodiments of the invention.

FIG. 2 shows a lens layout and ray tracing for a high magnification indirect ophthalmoscopy lens device according to another embodiment of the invention. According to this embodiment there is provided a biconvex first lens 20 which may be aspheric on both surfaces 2b, 3b. An anterior lens 22 is spaced in an anterior direction from first lens 20 relative to the pupillary plane P. Anterior lens 22 has a concave posterior surface 4b which may be spherical. Anterior lens 22 has a convex anterior surface 5b which may be aspherical. Table II below shows an example of the characteristics of the lenses and lens surfaces as well as the spacing of the lenses.

TABLE II

| Surface | Radius (mm) | Conic Constant | Distance From Corneal Apex (mm) | Diameter (mm) |
| --- | --- | --- | --- | --- |
| 2b | 18.44891 | −1.44 | 8.000000 | 20.0 |
| 3b | 25.0 | −1.462097 | 13.000000 | 20.0 |
| 4b | −40.0 | 0 | 29.000000 | 31.0 |
| 5b | 16.0 | −0.9 | 48.000000 | 31.0 |

In this example, all lenses are also made of PMMA acrylic plastic having an index of refraction of 1.491. As in the lens device of FIGS. 1, 1A and 1B, the diverging chief rays produce a magnified real image. In this case, the real image is in a curved plane $I_1$ which is located wholly within anterior lens 22. The real image is again not adequately viewable without the assistance of the anterior lens element which serves to direct the chief rays toward the slit-lamp collection lens so that the image can be observed binocularly. As in the prior embodiments, the viewed image is a further magnified virtual image in plane $V_I$ spaced from the corneal apex by a distance of 36.879 mm in the example provided by Table II.

Figure 3:
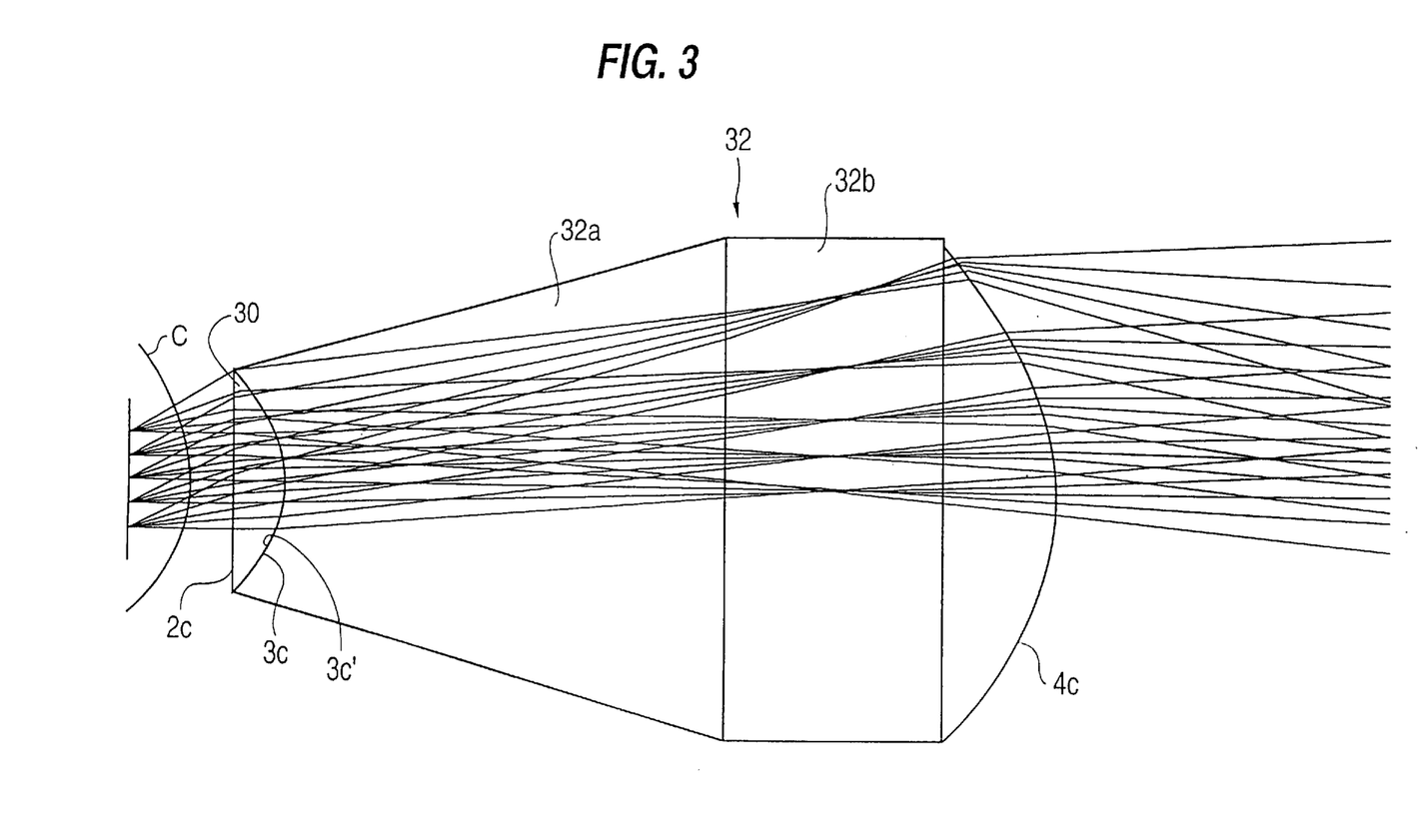

FIG. 3 illustrates a lens layout and ray tracing according to yet another embodiment of the invention. This embodiment utilizes a compound lens system comprising a plano convex lens portion 30 made for example of LAH 58 glass having a convex anterior surface 3c cemented to a substantially mating concave surface 3c' of a generally frusto-conical portion 32a of PMMA acrylic body 32.

The PMMA acrylic body 32 includes a cylindrical section 32b capped with a convex anterior surface 4c. Table III below lists specifications of an example for implementing the embodiment according to FIG. 3. In this embodiment, both the real and virtual images are produced within acrylic body 32.

TABLE III

| Surface | Radius (mm) | Conic Constant | Distance From Corneal Apex (mm) | Diameter (mm) |
|---|---|---|---|---|
| 2c | 1Infinity | 0 | 2.000000 | 11.0 |
| 3c | 7 | −0.5359154 | 4.300000 | 11.0 |
| 3c' | −7 | −0.5359154 | 4.300000 | 11.0 |
| 4c | 12.5 | −0.7 | 39.300000 | 22.0 |

Figure 4:
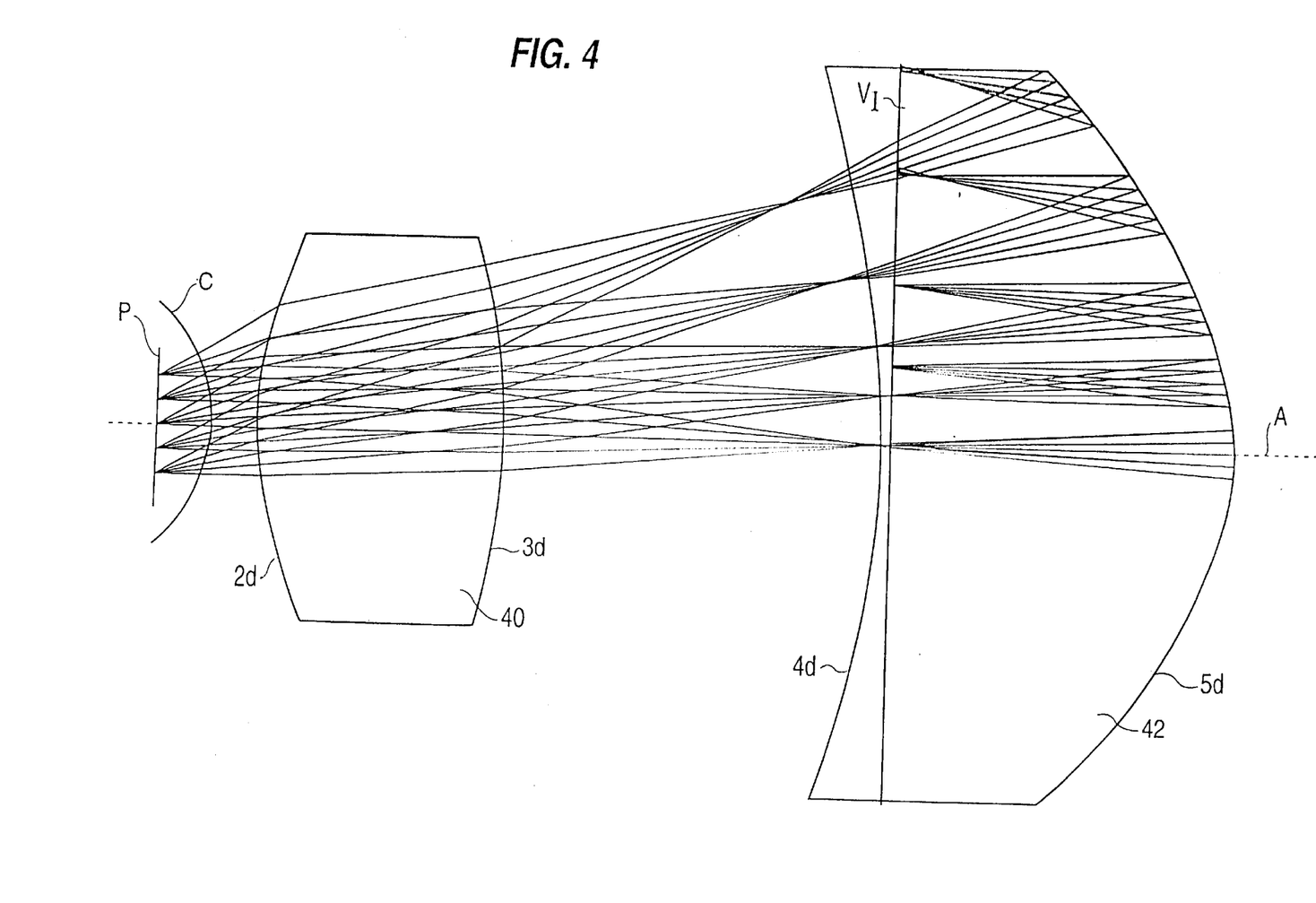

FIG. 4 shows a further embodiment of a high magnification indirect ophthalmoscopy lens device constructed in accordance with the principles of the invention. This embodiment employs a biconvex first lens 40 for producing the real image and a concave-convex anterior lens which bends the light rays toward the pupil aperture of the slit-lamp biomicroscope as previously discussed. In this embodiment, the real image is formed in air between the first and anterior lenses 40, 42, and the virtual image is formed in plane $V_I$ located wholly within the anterior lens 42. First lens 40 has posterior and anterior surfaces 2d, 3d, respectively, and anterior lens 42 has posterior and anterior surfaces 4d, 5d, respectively. Table IV below provides an example of the lens and surface characteristics of the lenses and the distances of the surfaces relative to the corneal apex which would result in the illustrated ray tracing that produces the virtual image in plane $V_I$ as shown in FIG. 4, which according to this example is spaced approximately 33 mm from the corneal apex.

TABLE IV

| Surface | Radius (mm) | Conic Constant | Distance From Corneal Apex (mm) | Diameter (mm) |
|---|---|---|---|---|
| 2d | 16.96 | −1.3456 | 3.000000 | 18.0 |
| 3d | 27.29 | −5.76 | 15.000000 | 18.0 |
| 4d | −40.00 | 0 | 32.000000 | 31.0 |
| 5d | 14.00 | −.77 | 49.000000 | 31.0 |

FIGS. 5–8 illustrate additional non-limiting, embodiments which show that the principles of the invention can also be implemented in combination with a contact lens element. Tables V through VIII below illustrate specific examples for implementing each of the embodiments in FIGS. 5–8, respectively.

Figure 5:
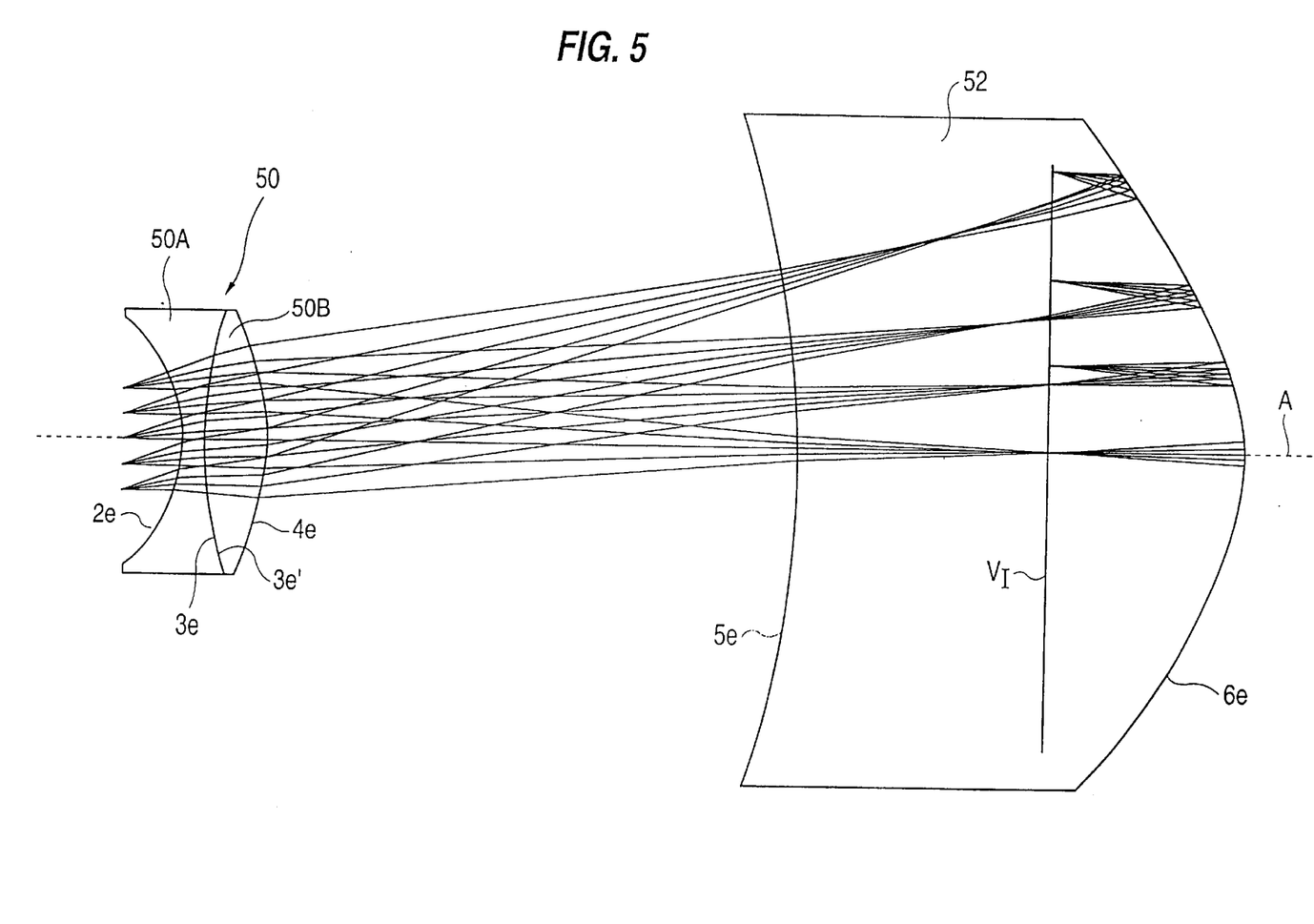

Briefly, FIG. 5 employs a compound contact lens element which may be constructed in accordance with the principles described in my prior U.S. Pat. No. 5,523,810, the subject matter of which is incorporated herein by reference. In this embodiment, a compound contact lens element 50 comprises a biconcave posterior portion 50A and a biconvex anterior portion 50B. Lens element 50 has a posterior surface 2e, matching mating surfaces 3e' and 3e, and an anterior surface 4e. An anterior lens element 52 has a concave posterior surface 5e and a convex anterior surface 6e. Both the real image and virtual image are produced in anterior lens element 52. Table V below presents exemplary characteristics that may be used to implement this embodiment, wherein posterior portion 50A and lens 52 are made of PMMA acrylic plastic and anterior portion 50B is made of LAH 58 glass. Surface 4e may desirably be optimized with high order deformation terms as is known in the art.

TABLE V

| Surface | Radius (mm) | Conic Constant | Distance From Corneal Apex (mm) | Diameter (mm) |
|---|---|---|---|---|
| 2e | −7.55 | −0.18 | 0.000000 | 12.0 |
| 3e' | −20.00 | 0 | 1.000000 | 12.7 |
| 3e | 20.00 | 0 | 1.000000 | 12.7 |
| 4e | 12.27814 | −1.419892 | 4.000000 | 12.7 |
| 5e | −40.00 | 0 | 29.000000 | 28.0 |
| 6e | 13.20 | −0.76 | 50.000000 | 28.0 |

Figure 6:
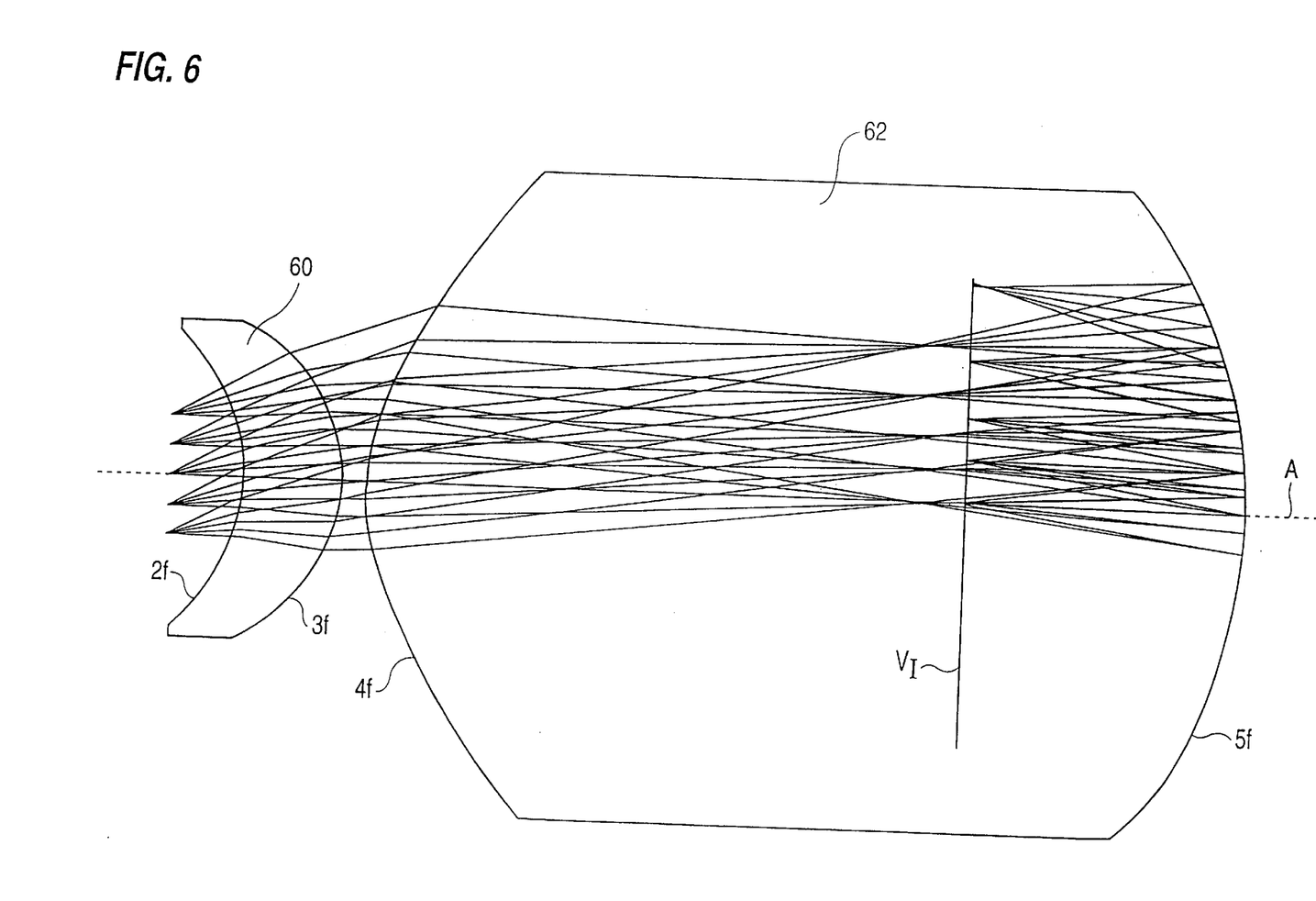

In FIG. 6, a meniscus-type contact lens element 60 is used in combination with an elongated biconvex lens element 62, for producing both the real and virtual images within lens element 62. Table VI below presents exemplary characteristics that may be used to implement this embodiment wherein both lens 60 and 62 are made of PMMA acrylic plastic.

TABLE VI

| Surface | Radius (mm) | Conic Constant | Distance From Corneal Apex (mm) | Diameter (mm) |
|---|---|---|---|---|
| 2f | −7.55 | −0.18 | 0.000000 | 12.00 |
| 3f | 6.918643 | 0.03810126 | 4.000000 | 12.70 |
| 4f | 10.23489 | −1.000000 | 5.000000 | 23.00 |
| 5f | 18.00 | 0.9574642 | 40.000000 | 23.00 |

Figure 7:
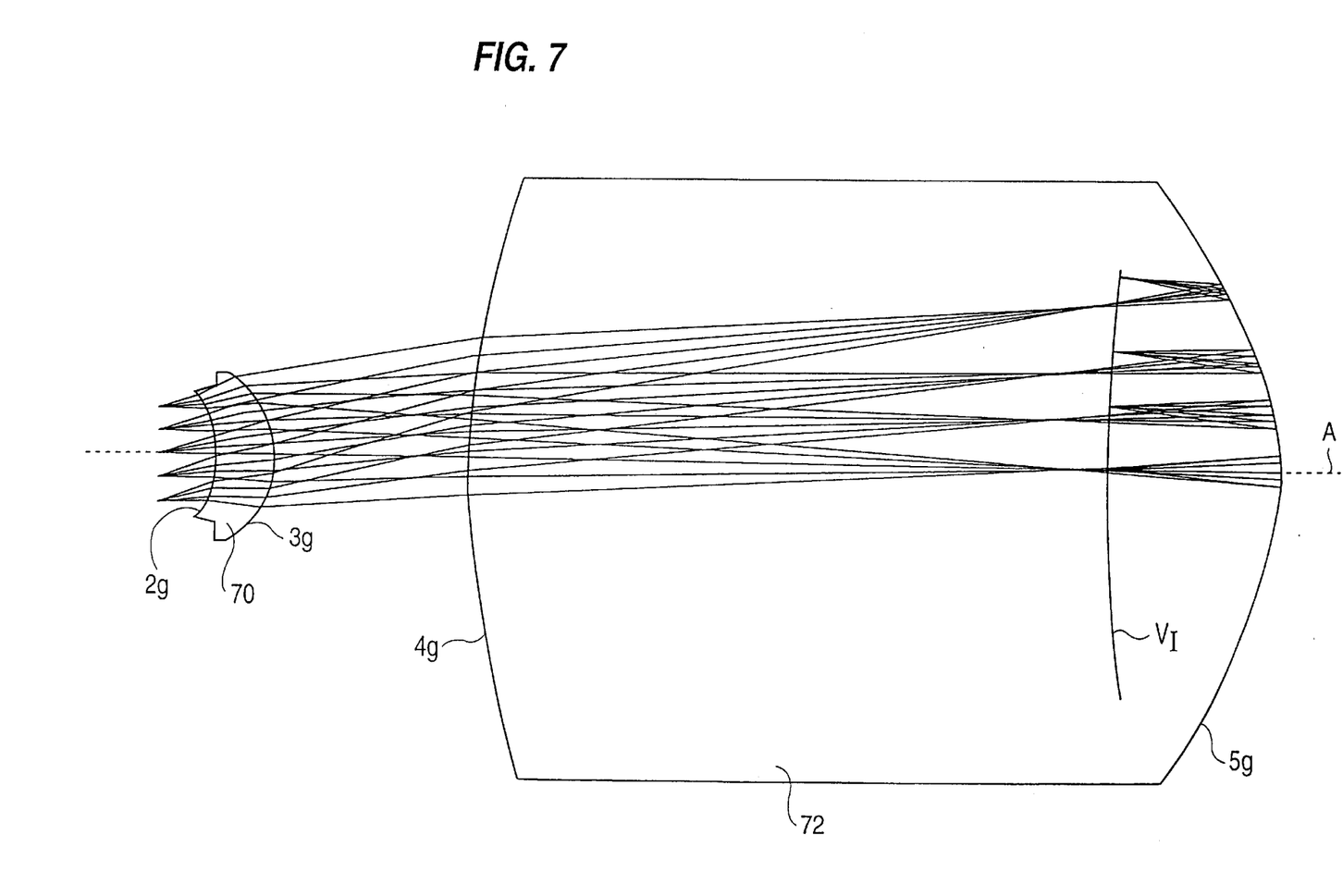

FIG. 7 includes a meniscus contact lens element 70 and a biconvex lens 72. With the exemplary characteristics for surfaces 2g–5g shown in Table VII below and both lens elements being made of PMMA acrylic plastic, a slightly concave virtual image in plane $V_I$ is located wholly within lens element 72.

TABLE VII

| Surface | Radius (mm) | Conic Constant | Distance From Corneal Apex (mm) | Diameter (mm) |
|---|---|---|---|---|
| 2g | −8.00 | 3.950734 | 0.000000 | 9.00 |
| 3g | 6.451816 | 0.8668565 | 3.000000 | 9.00 |
| 4g | 40.00000 | 0 | 13.000000 | 28.00 |
| 5g | 16.00 | −0.85 | 54.000000 | 28.00 |

Figure 8:
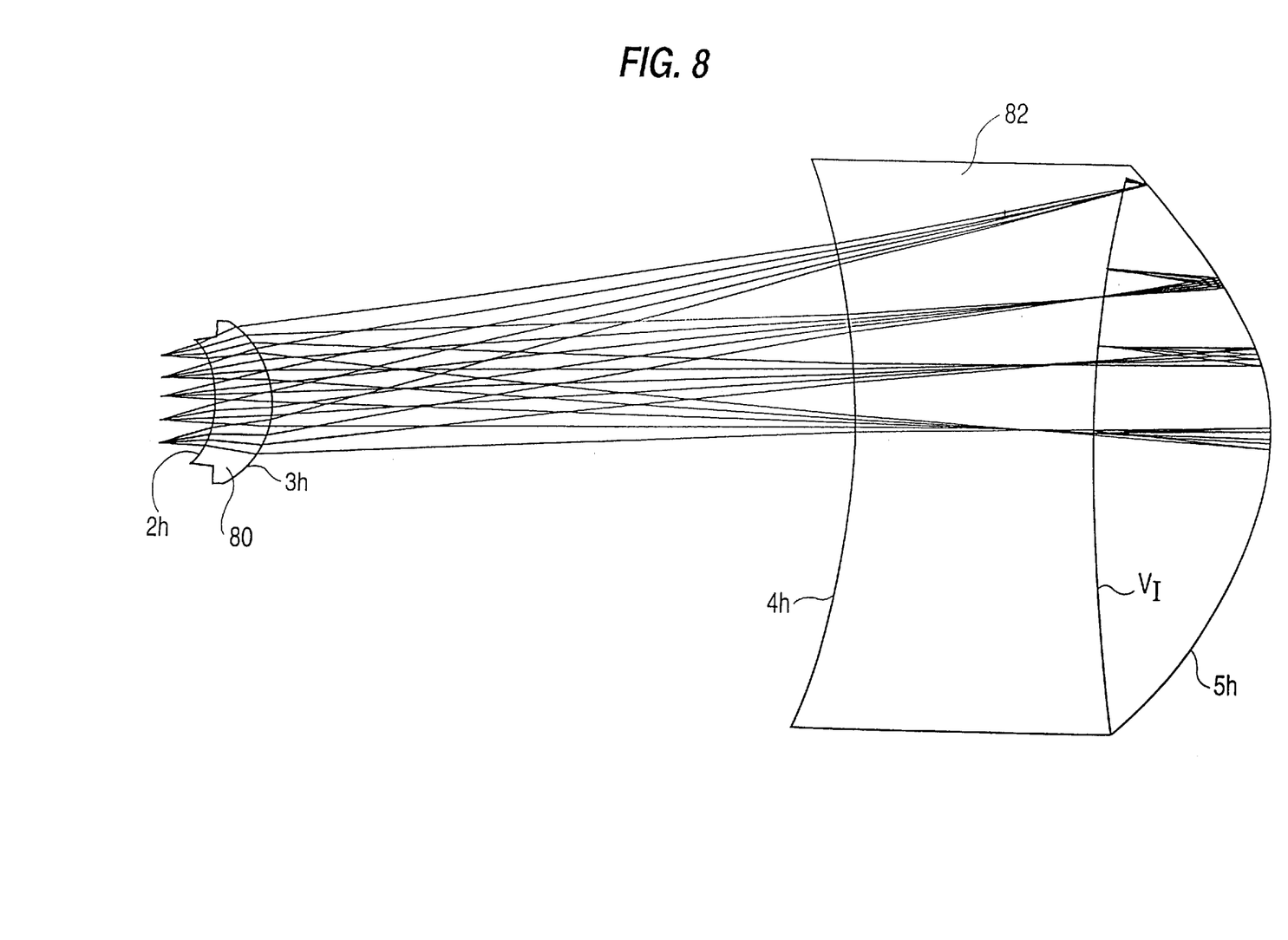

FIG. 8 shows a lens layout including a meniscus contact lens element 80 and an anterior concave-convex lens element 82. With the exemplary characteristics present in Table VIII below for surfaces 2h–5h and both lens elements being made of PMMA acrylic plastic, a slightly concave virtual image plane $V_I$ is presented wholly within lens 82.

TABLE VIII

| Surface | Radius (mm) | Conic Constant | Distance From Corneal Apex (mm) | Diameter (mm) |
| --- | --- | --- | --- | --- |
| 2h | −8.00 | 3.950734 | 0.000000 | 9.00 |
| 3h | 6.451816 | 0.8668565 | 3.000000 | 9.00 |
| 4h | −40.00000 | 0 | 33.000000 | 28.00 |
| 5h | 13.80 | −0.76 | 54.000000 | 28.00 |

Figure 9:
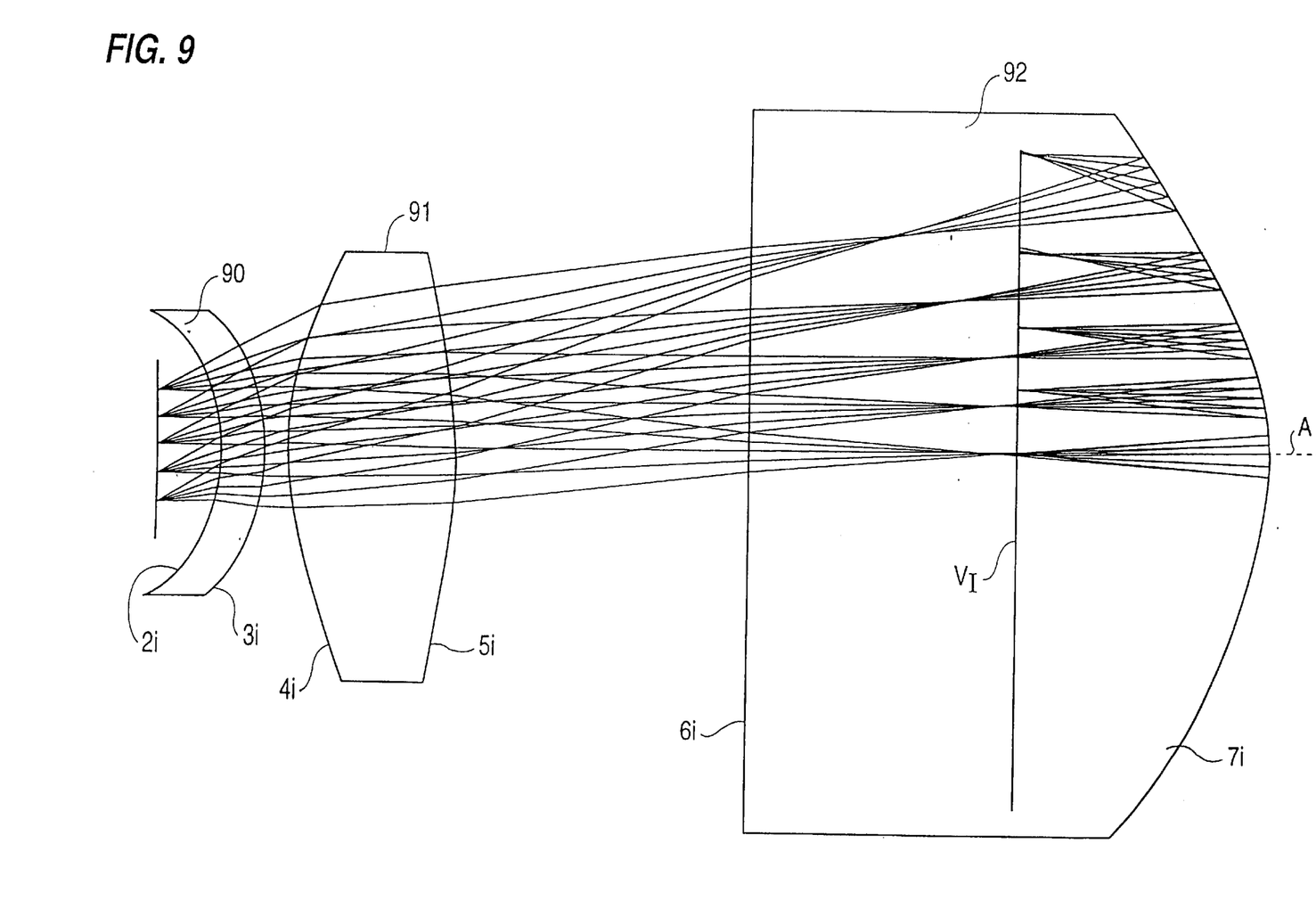

FIG. 9 illustrates a three element system including a meniscus contact lens element 90, a biconvex middle element 91, and a plano-convex anterior element 92. Table IX gives exemplary characteristics for surfaces $2i$–$7i$ that result in a virtual image in plane $V_I$ located within anterior element 92. In this example, the lens elements are again made of PMMA acrylic plastic.

TABLE IX

| Surface | Radius (mm) | Conic Constant | Distance From Corneal Apex (mm) | Diameter (mm) |
| --- | --- | --- | --- | --- |
| 2i | −7.55 | −0.18 | 0.000000 | 12.70 |
| 3i | 9.20 | 0 | 2.000000 | 12.70 |
| 4i | 15.146 | −1.4874 | 3.000000 | 18.00 |
| 5i | 24.3653 | −11.84637 | 10.500000 | 18.00 |
| 6i | Infinity | 0 | 23.300000 | 28.00 |
| 7i | 15.00 | −0.80 | 45.900000 | 28.00 |

The foregoing embodiments and specific examples thereof illustrate that a variety of embodiments are possible for implementing the principles of the invention. Briefly stated, the indirect ophthalmoscopy lens device of the invention may either be of the contact or non-contact type wherein the lenses of the device are designed to produce both a real and virtual image posterior to the anterior-most surface of the device. The direction of the chief rays toward the real image are divergent, thus allowing increased magnification in the system as illustrated in FIGS. 1 through 9. The anterior lens with its convex anterior lens surface further increases magnification by refracting the divergent chief rays in the direction of the collection lens of a slit-lamp biomicroscope. The high image magnification and resolution make the device ideal for extremely detailed diagnosis and very exacting laser treatment in critical areas near the macula, which is the most light sensitive portion of the eye.

The invention is not limited to any of the embodiments or specific examples described herein.

It is possible, for example, to combine any embodiments of the invention with the use of a reticle in the plane of the real image for making measurements of structures in the real image. A similar use of a reticle is disclosed in my prior U.S. Pat. No. 5,255,025.

In yet another variation within the scope of the invention, the anterior lens need not be mounted in a fixed relationship with respect to the first lens and/or a contact lens. The anterior lens may, for example, be mounted on the end of a biomicroscope and thus be movable along and transverse the optical axis with respect to the first (imaging) lens and/or a contact lens element.

In further variations of the invention, the image forming first lens, for example lens 10, 20, 30 or 40 in FIGS. 1–4, may comprise an image forming lens system including a plurality of lenses which cooperate to form an image of the patient's fundus outside of the eye in a manner known to those skilled in the art.

The invention has been described in detail with respect to preferred embodiments, and it will now be apparent from the foregoing to those skilled in the art that changes and modifications may be made without departing from the invention in its broader aspects, and the invention, therefore, as defined in the appended claims is intended to cover all such changes and modifications as fall within the true spirit of the invention.

What is claimed is:

1. An indirect ophthalmoscopy lens device for use with a slit-lamp or other biomicroscope in an examination, laser treatment or surgical treatment of a patient's eye, comprising:

an image forming lens system for collecting and focussing light exiting a patient's eye to form a real image of the fundus of the patient's eye at a location outside the eye; and an anterior lens having a convex anterior surface and being disposed anterior to the image forming lens system so that the real image formed by the image forming lens system is located posterior of the convex anterior surface, the convex anterior surface of the anterior lens refracting chief rays of respective light ray bundles of the light exiting the patient's eye generally toward a collecting lens of the slit-lamp or other biomicroscope, whereby an image viewed through the slit-lamp or other biomicroscope comprises a virtual image that has a positive magnification relative to the real image formed by the image forming lens system and relative to the fundus of the patient's eye.

2. The indirect ophthalmoscopy lens system according to claim 1, wherein the chief rays proceeding from the image forming lens system diverge from one another toward the real image.

3. The indirect ophthalmoscopy lens system according to claim 1, wherein the image forming lens system is constructed and spaced apart from the anterior lens so that the real image is produced at least partially in the anterior lens.

4. The indirect ophthalmoscopy lens system according to claim 1, wherein the image forming lens system is constructed and spaced apart from the anterior lens so that the real image is produced posterior to the anterior lens.

5. The indirect ophthalmoscopy lens system according to claim 1, wherein the anterior lens is constructed so that light rays are refracted by the convex anterior surface to produce the virtual image in the anterior lens.

6. The indirect ophthalmoscopy lens system according to claim 1, wherein the anterior lens is constructed so that light rays are refracted by the convex anterior surface to produce the virtual image posterior to the anterior lens.

7. The indirect ophthalmoscopy lens system according to claim 1, wherein the anterior lens has a planar posterior surface.

8. The indirect ophthalmoscopy lens system according to claim 1, wherein the anterior lens has a concave posterior surface.

9. The indirect ophthalmoscopy lens system according to claim 1, wherein the anterior lens has a convex posterior surface.

10. The indirect ophthalmoscopy lens system according to claim 1, wherein the image forming lens system includes a biconvex lens.

11. The indirect ophthalmoscopy lens system according to claim 10, wherein the biconvex lens has posterior and anterior surfaces, and the posterior surface is more steeply curved than the anterior surface.

12. The indirect ophthalmoscopy lens system according to claim 11, wherein the posterior surface of the biconvex lens is spherical and the anterior surface of the biconvex lens is aspheric.

13. The indirect ophthalmoscopy lens system according to claim 12, wherein the anterior surface of the biconvex lens is an aspheric conoid.

14. The indirect ophthalmoscopy lens system according to claim 1, wherein the convex anterior surface of the anterior lens is aspheric.

15. The indirect ophthalmoscopy lens system according to claim 14, wherein the convex anterior surface of the anterior lens is an aspheric conoid.

16. The indirect ophthalmoscopy lens system according to claim 1, wherein the image forming lens system comprises a contact lens element having a concave posterior surface adapted to be placed on the cornea of a patient's eye.

17. The indirect ophthalmoscopy lens system according to claim 16, wherein the contact lens element is a compound lens having posterior and anterior lens portions which have complementary mating surfaces that are fixed together.

18. The indirect ophthalmoscopy lens system according to claim 1, wherein the image forming lens system includes an imaging lens arrangement and a contact lens element located posterior to and coaxial with the imaging lens arrangement, the contact lens element having a concave posterior surface adapted to be placed on the cornea of a patient's eye.

19. The indirect ophthalmoscopy lens system according to claim 18, wherein the imaging lens arrangement includes a biconvex lens.

20. The indirect ophthalmoscopy lens system according to claim 19, wherein the anterior lens has a concave posterior surface.

21. The indirect ophthalmoscopy lens system according to claim 19, wherein the anterior lens has a planar posterior surface.

22. The indirect ophthalmoscopy lens system according to claim 1, further including a frame mounting the image forming lens system and anterior lens to be coaxial with one another.

* * * * *